(12) United States Patent
Patterson (10) Patent No.: US 11,628,122 B2
(45) Date of Patent: Apr. 18, 2023

(54) SYSTEM AND METHOD FOR TRACKING MEDICAL EXPIRATION DATES

(71) Applicant: Tamia Myshia Patterson, Staten Island, NY (US)

(72) Inventor: Tamia Myshia Patterson, Staten Island, NY (US)

(*) Notice: Subject to any disclaimer, the term of this patent is extended or adjusted under 35 U.S.C. 154(b) by 0 days.

(21) Appl. No.: 17/025,967

(22) Filed: Sep. 18, 2020

(65) Prior Publication Data

US 2022/0087903 A1   Mar. 24, 2022

(51) Int. Cl.
*A61J 7/04*    (2006.01)
*G16H 40/67*  (2018.01)
*G16H 20/17*  (2018.01)

(52) U.S. Cl.
CPC .............. *A61J 7/04* (2013.01); *G16H 20/17* (2018.01); *G16H 40/67* (2018.01); *A61J 2205/10* (2013.01); *A61J 2205/30* (2013.01); *A61J 2205/60* (2013.01)

(58) Field of Classification Search
CPC ...... A61J 7/04; A61J 2205/10; A61J 2205/30; A61J 2205/60; G16H 20/13; G16H 20/17; G16H 40/67; G16H 70/40
See application file for complete search history.

(56) References Cited

U.S. PATENT DOCUMENTS

| | | | |
|---|---|---|---|
| 10,918,570 B1* | 2/2021 | Hincher, Sr. | A61J 1/00 |
| 2009/0265967 A1* | 10/2009 | Kaufman | G09F 3/0289 |
| | | | 40/310 |
| 2011/0220713 A1* | 9/2011 | Cloninger | G09F 3/0288 |
| | | | 235/375 |
| 2013/0161207 A1* | 6/2013 | Luciano, Jr. | A61J 1/03 |
| | | | 53/467 |

* cited by examiner

*Primary Examiner* — Orlando Bousono (57) ABSTRACT

An injectable medication tab used to track expiration dates has an informative tab, a release string, an adhesive liner, and a quick release fastener. The informative tab provides visually accessible information about a bottle to which the injectable medication tab is attached. An expiration information portion of the informative tab protrudes from the exterior surface of the bottle after being opened. The adhesive liner is superimposed onto a mounting surface of the informative tab and attaches the informative tab to the bottle. The quick release fastener is a coupling mechanism that connects between an edge of the informative tab and the release string. The release string forms a detachable connection holding the expiration information portion against the bottle until the bottle is opened. Once opened, the expiration information section to protrudes from the bottle until the expiration information is recorded and the medical information portion is adhered to the bottle.

9 Claims, 12 Drawing Sheets

SYSTEM AND METHOD FOR TRACKING MEDICAL EXPIRATION DATES

FIELD OF THE INVENTION

The present invention relates generally to medication packaging. More specifically, the present invention relates to a system that tracks expiration date information and promotes date recording compliance.

BACKGROUND OF THE INVENTION

Injectable medications are a common form of dispensing medication to a patient and come in both single and multiple dose bottles. In accordance with the American Hospital Association, all multiple dose injectable medications must be dated immediately after opening with both the date opened and expiration date. This policy has been instituted as to ensure that patients do not receive out-dated medications, which can prove harmful or even fatal to a patient. In addition to the dangers imposed upon patients, improper dating of medications can lead to fines by the American Hospital Association or the Occupational Safety and Health Administration during medical facility inspections. The two methods currently used to date multiple dose injectable medications are writing directly on the label of the medication bottle and using a color code system. The color code system can be confusing and time consuming as practitioners must remember the color associated with each month or year. Writing directly on the label is often difficult due to the curved nature of the bottles that medications are packaged in. This often results in illegible writing, making it difficult for others to decipher whether or not a medication has expired. Additionally, due to the nature of the material used to manufacture the medication labels, the written dates often smear or rub off completely. Again, this results in questionable medication dates causing medication to be thrown out or improperly administered. Another issue with dating medications is failure to remember to date a medication by the medical practitioner or medication administer.

Therefore it is the object of the present invention to provide an injectable medication date tab which makes itself visible when an injectable medication bottle is opened. This ensures that the medical practitioner or medication administer remembers to properly date the medication. The injectable medication date tab extends from the medication bottle and allows the user to place the medication label on a flat surface such that dates can readily and legibly be written. Once the medication bottle has been properly dated an adhesive backing allows the injectable medication date tab to be reattached to the surface of the medication bottle. The injectable medication date tab is also smear proof such that dates will not rub off resulting in unknown expiration dates.

DETAIL DESCRIPTIONS OF THE INVENTION

All illustrations of the drawings are for the purpose of describing selected versions of the present invention and are not intended to limit the scope of the present invention.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure.

Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification, and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate. As used herein, the term "dorsal" refers to positions that are located near, on, or towards the upper or top side of a structure.

The present disclosure includes many aspects and features. Moreover, while many aspects and features relate to, and are described in the context of detection of presence of one or more intruder devices, embodiments of the present disclosure are not limited to use only in this context.

Referring to FIG. 1 through FIG. 12, the present invention is an injectable medication date tab that enables a medical professional to quickly inspect and record information relating to the contents of a medication bottle. As a side note, the term medical professional is used herein to refer to any individual authorized to view or engage in activities including, but not limited to, medical procedures, medical data analysis, and medical patient care. The present invention is designed to provide a system and apparatus for recording the time that a bottle of injectable medication is opened and when the opened bottle will expire. To achieve this functionality, the present invention employs the injectable medication date tab as a component of a system for tracking medication expiration dates. The system employs an informative label that is attached to the medication bottle. A quick release mechanism to integrated into the label such that a tab is flipped away from the medication bottle whenever the medication bottle is first opened by the medical professional. The upturned tab functions as a reminder that instructs the medical professional to record the date the medication bottle is opened and the date the medication will expire. While the disclosure is primarily directed toward recording and monitoring the expiration dates of injectable medications, it is to be understood that the system and apparatus provided by the present invention is intended to be adapted to any number of research and inventory management tasks including, but not limited to, specimen tracking, materials management, and patient prescription usage tracking. Additionally, the term medication bottle can be broadly interpreted to refer to any container housing material that may or may not have an expiration date.

Figure 6:
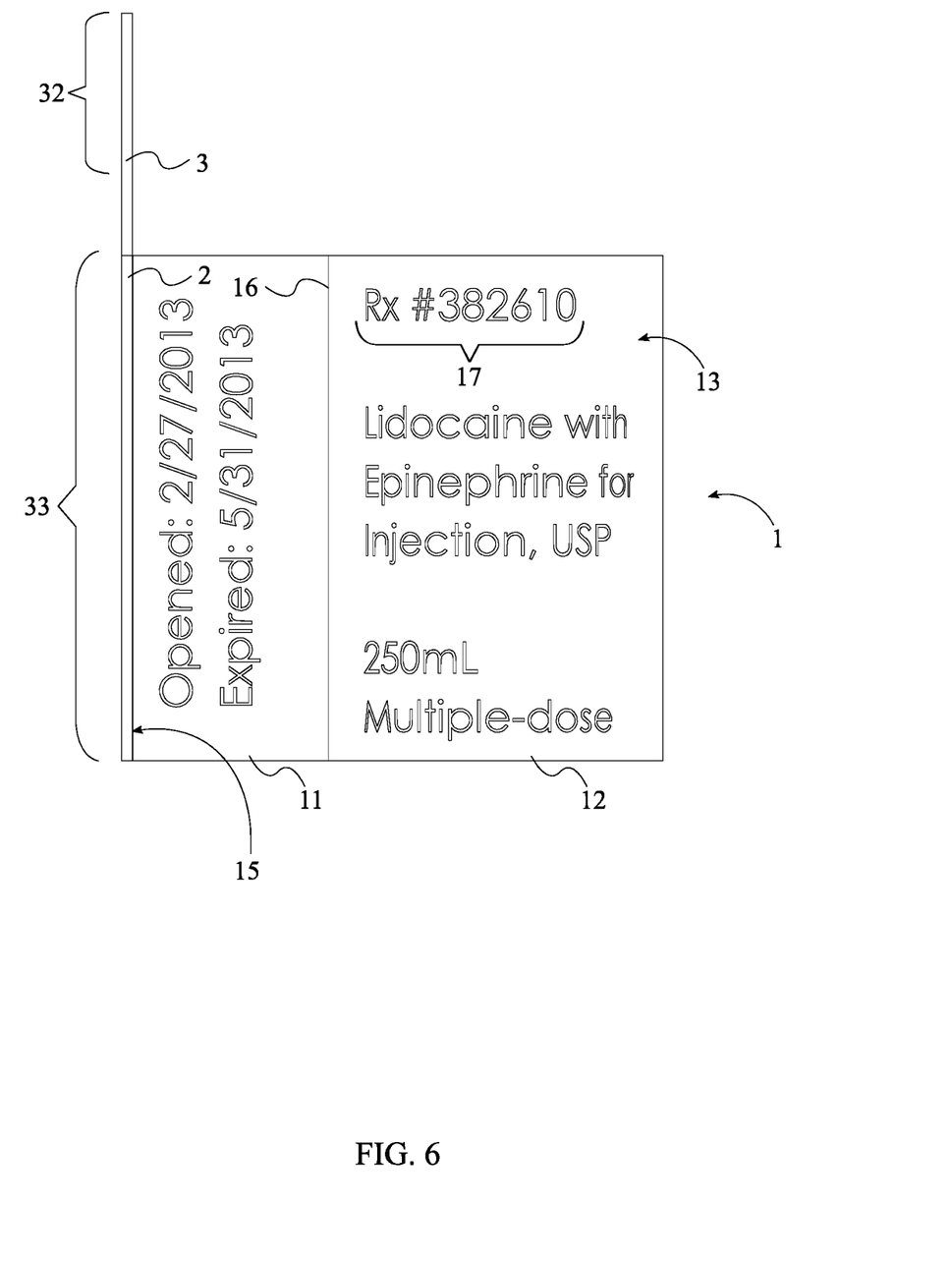
FIG. 6 is a front view of the present invention.
Figure 7:
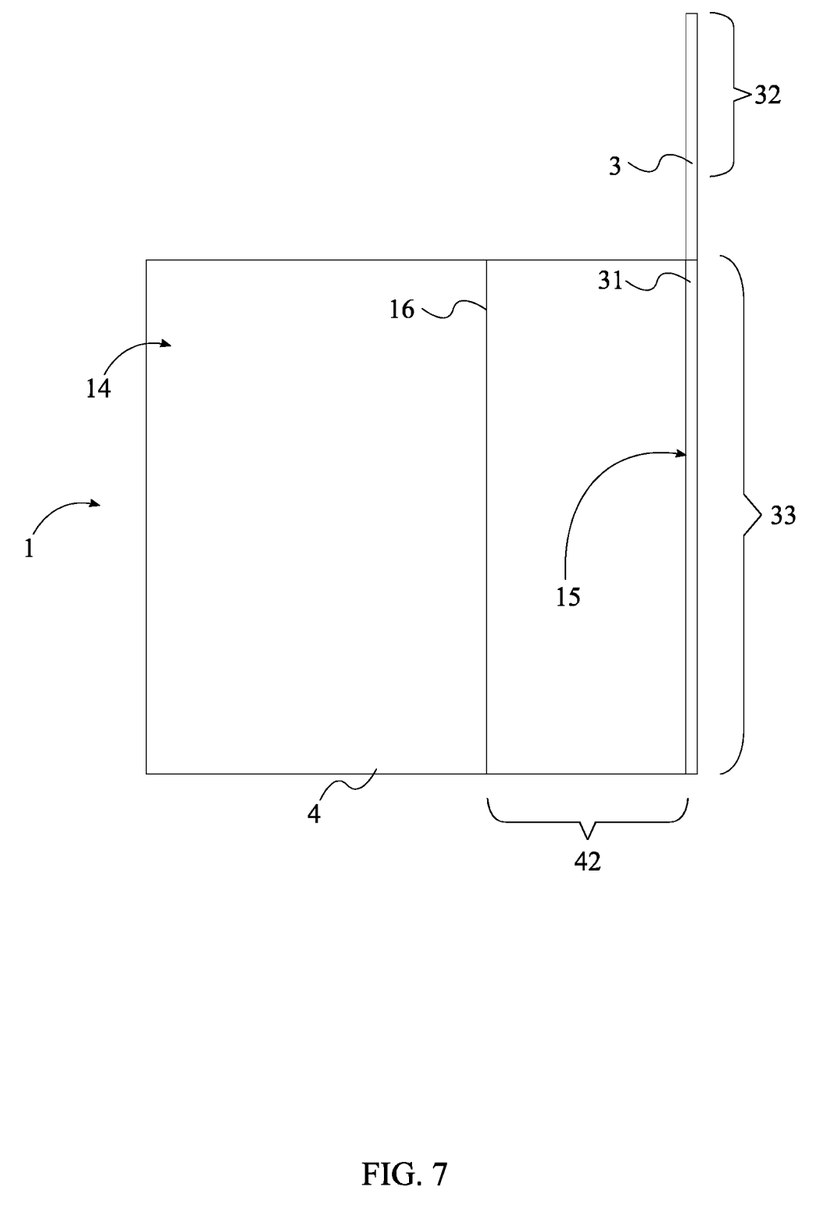
FIG. 7 is a rear view of the present invention.

Referring to FIG. 6 and FIG. 7, as described above, the present invention employs the injectable medication date tab to provide a tool for prompting adherence to quality assurance standards and for facilitating visual records keeping. To achieve this functionality, the present invention comprises an informative tab 1, a release string 3, an adhesive liner 4 and a quick release fastener 2. The informative tab 1 functions as a multicomponent label that is attached to an exterior surface of the medication bottle. Specifically, the informative tab 1 comprises an expiration date portion 11 and a medical information portion 12 that are used to visually output medication information. The expiration date portion 11 is positioned adjacent to the medical information portion 12 across a labeling surface 13 of the informative tab 1. As a result, the present invention provides a standardized arrangement of information for the medical professional to visually inspect. The expiration date portion 11 is a surface on which the medical professional is encouraged to record the date that the medication bottle was opened as well as the date that the medication contained within will expire. The medical information portion 12 is a section of the informative tab 1 that is designed to provide a visual record of information pertinent to the contents of the medication bottle. The adhesive liner 4 is a fastening mechanism used to bond the informative tab 1 to an external surface. Additionally, the adhesive liner 4 is superimposed onto a mounting surface 14 of the informative tab 1. Further, the mounting surface 14 is positioned opposite to the labeling surface 13 across the informative tab 1. Thus configured, the adhesive liner 4 and the mounting surface 14 enable the expiration date portion 11 and the medical information portion 12 to be oriented away from the medication bottle when the informative tab 1 is attached to the medication bottle.

Figure 1:
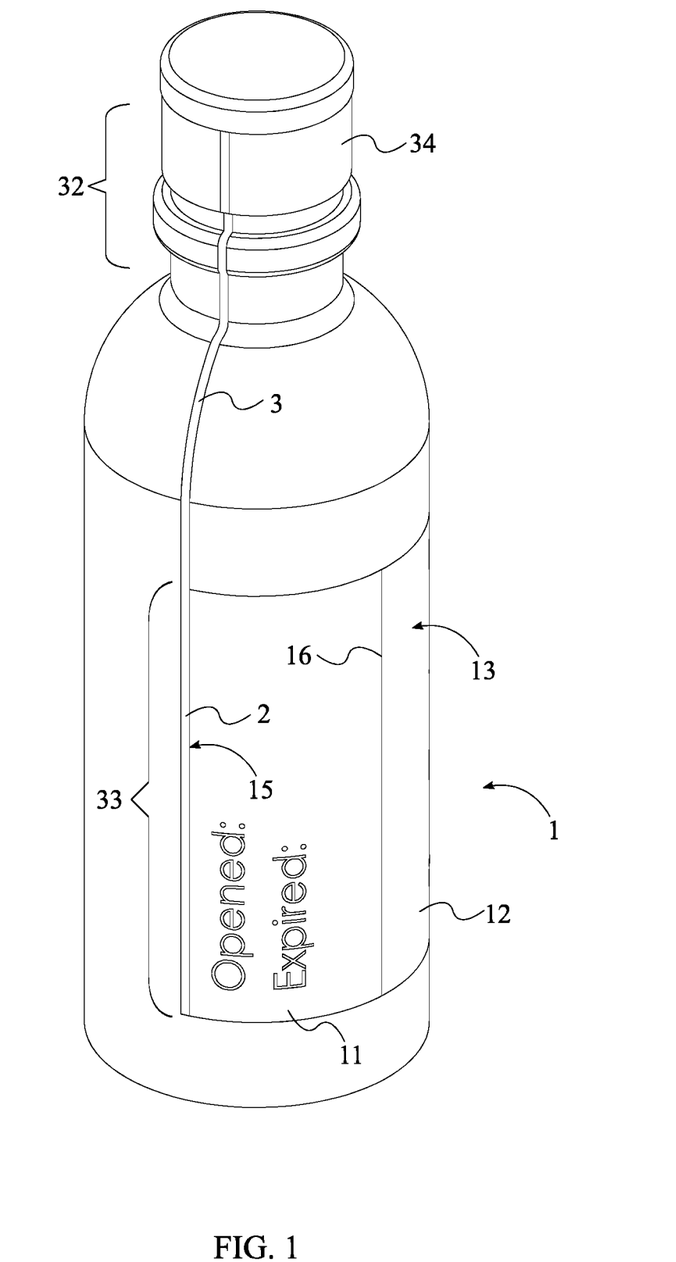
FIG. 1 is a perspective view of the present invention attached to a bottle of medication.
Figure 3:
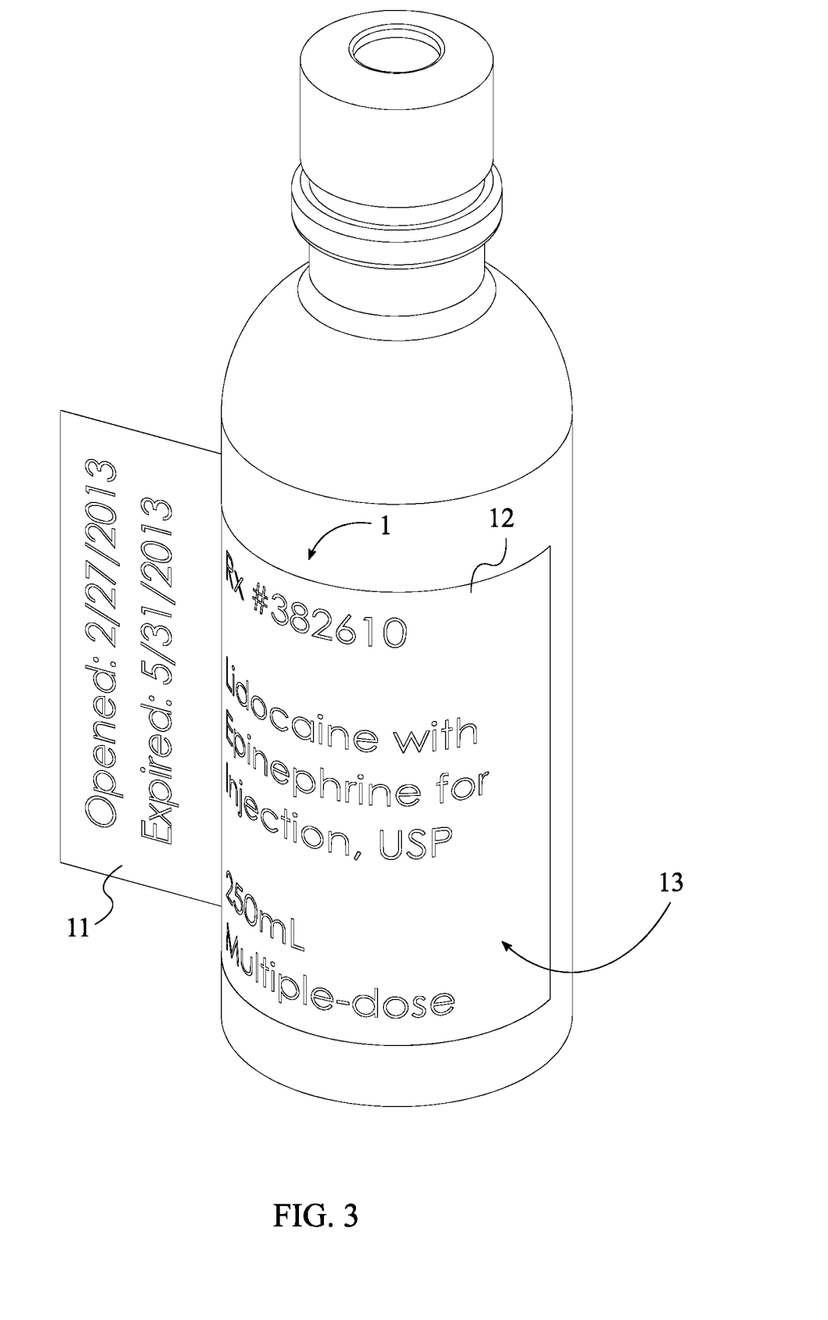
FIG. 3 is a front perspective view of the present invention with the medical information portion protruding from the medication bottle.

Referring to FIG. 1 and FIG. 3, the quick release fastener 2 is a device that forms a semi-permanent seal and coupler which persists until broken. Further, the quick release fastener 2 is connected in between the release string 3 and a widthwise edge 15 of the informative tab 1. Thus connected, the quick release fastener 2 retains the expiration date portion 11 adjacent to the surface of the medication bottle until the release string 3 is decoupled from the quick release fastener 2. As the release string 3 is decoupled from the quick release mechanism, the expiration date portion 11 if propelled away from the medication bottle. In some embodiments, the quick release fastener 2 is a perforated connection between the release string 3 and the widthwise edge 15. Additional embodiments may be designed with quick release fasteners 2 selected from the group including, but not limited to magnetic couplers, scored strips of material, and adhesives. Preferably, the expiration date portion 11 of the informative tab 1 extends normal to the exterior surface of the medication bottle after the release string 3 has been decoupled from the quick release fastener 2. This decoupling typically takes place when the medication bottle is opened, and thus the medical professional opening the medication bottle is reminded to record the date of the opening and the expiration date of the medication.

Referring to FIG. 1, in some embodiments the quick release string 3 is designed to function as a tamper evident seal that indicates when the medication bottle has been opened. To achieve this functionality, the present invention comprises an adhesive strip 31 and a cap-securing seal 34. The adhesive strip 31 is superimposed along a tab-securing portion 33 of the release string 3 and is positioned opposite to the quick release fastener 2 across the tab-securing portion 33. Accordingly, the adhesive strip 31 serves to retain the widthwise edge 15 of the expiration date portion 11 flush against the exterior surface of the medication bottle until the release string 3 is decoupled from the quick release fastener 2. In further embodiments, the release string 3 comprises a cap tether 32 that is used to mate the informative tab 1 to the cap of the medication bottle. The cap tether 32 is positioned adjacent to the tab-securing portion 33 and thus extends between the widthwise edge 15 and the bottlecap. The cap-securing seal 34 forms a final coupling mechanism that binds the physical state of the bottlecap to the present invention. The cap tether 32 is integrated into the cap-securing seal 34 so that opening the medication bottle will cause the release string 3 to become decoupled from the quick release fastener 2. In some embodiments the cap-securing seal 34 is a tamper evident device that keeps the medication bottle closed and registers whenever the medication bottle is opened. For example, the sap-securing seal completes an alarm circuit whenever the medication bottle is opened.

Figure 4:
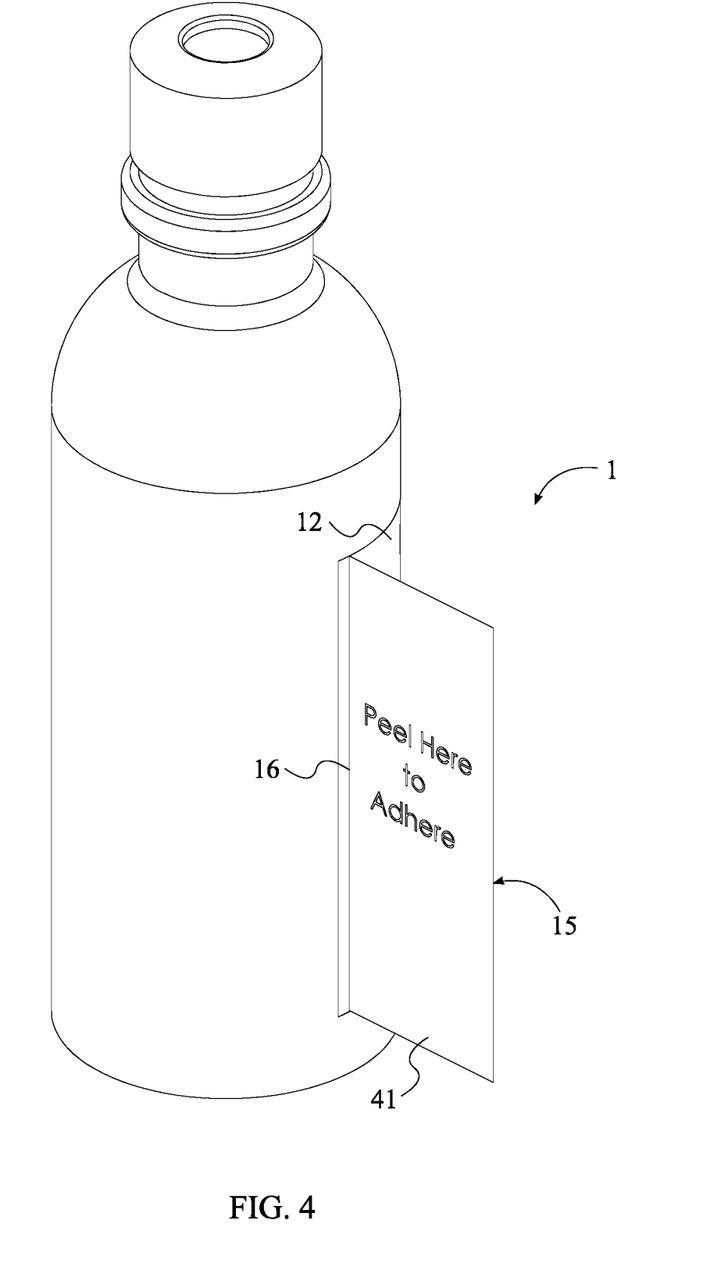
FIG. 4 is a rear perspective view of the present invention with the medical information portion protruding from the medication bottle.
Figure 5:
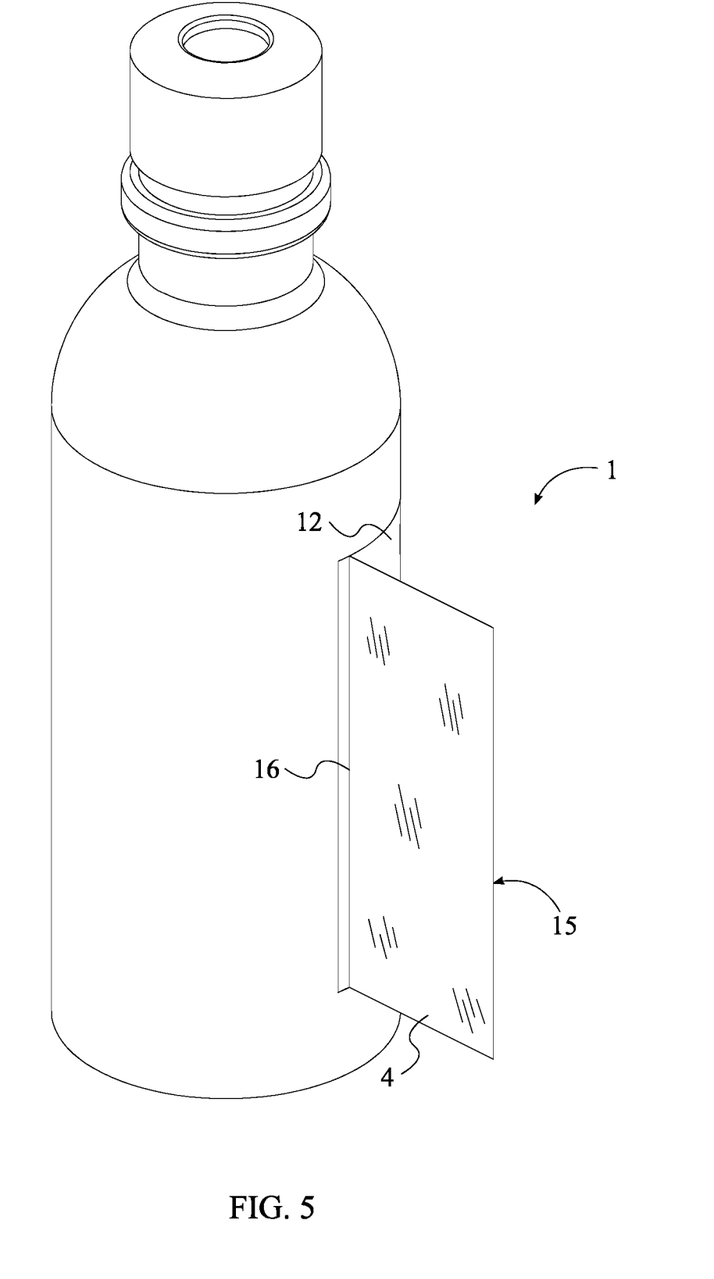
FIG. 5 is a rear perspective view of the present invention with the medical information portion protruding from the medication bottle and the adhesive protector removed.

Referring to FIG. 4, FIG. 6, and FIG. 7, because the present invention is designed to improve OA compliance and patient outcomes many quality of life improvements have been incorporated into the system. Namely, the present invention comprises a fold 16, an adhesive protector 41, at least one identifier (ID) token, and a wireless communication device 18. The fold 16 traverses across the informative tab 1 and is positioned in between the expiration date portion 11 and the medical information portion 12. Thus positioned, the fold 16 acts as a biasing spring for the expiration date portion 11 of the information tab and propels the expiration date portion 11 away from the medication bottle when the release string 3 is decoupled from the quick release fastener 2. Further, the fold 16 acts as a demarcation between the information displayed on the expiration date portion 11 and the medical information portion 12. The adhesive protector 41 is a flexible panel of material. The adhesive protector 41 is temporarily attached to a reattachment portion 42 of the adhesive liner 4. The reattachment portion 42 of the adhesive liner 4 is intended to enable the medical professional to resecure the expiration date portion 11 against the exterior surface of the medication bottle after the release string 3 has been decoupled from the quick release fastener 2. Preferably, the reattachment portion 42 is coextensive with the expiration date portion 11 so that the expiration date is portion can be readily manipulated while the adhesive protector 41 is in place and become fixedly attached to the medication bottle when the adhesive shield is removed. The intended use case involves the medical professional removing the adhesive protector 41 after opening the medication bottle and recording the relevant dates. The medical professional then presses the expiration date portion 11 against the medication bottle and the expiration date portion 11 is fixed in place.

Figure 2:
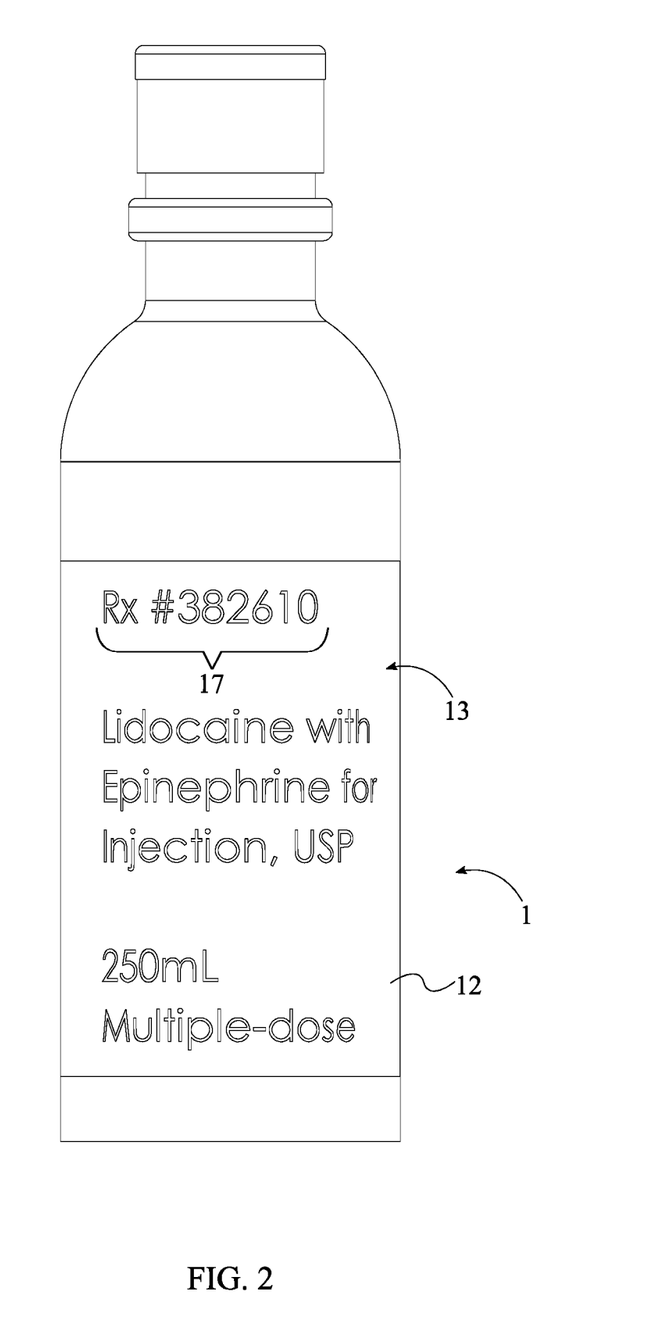
FIG. 2 is a front view of the present invention attached to a bottle of medication
Figure 8:
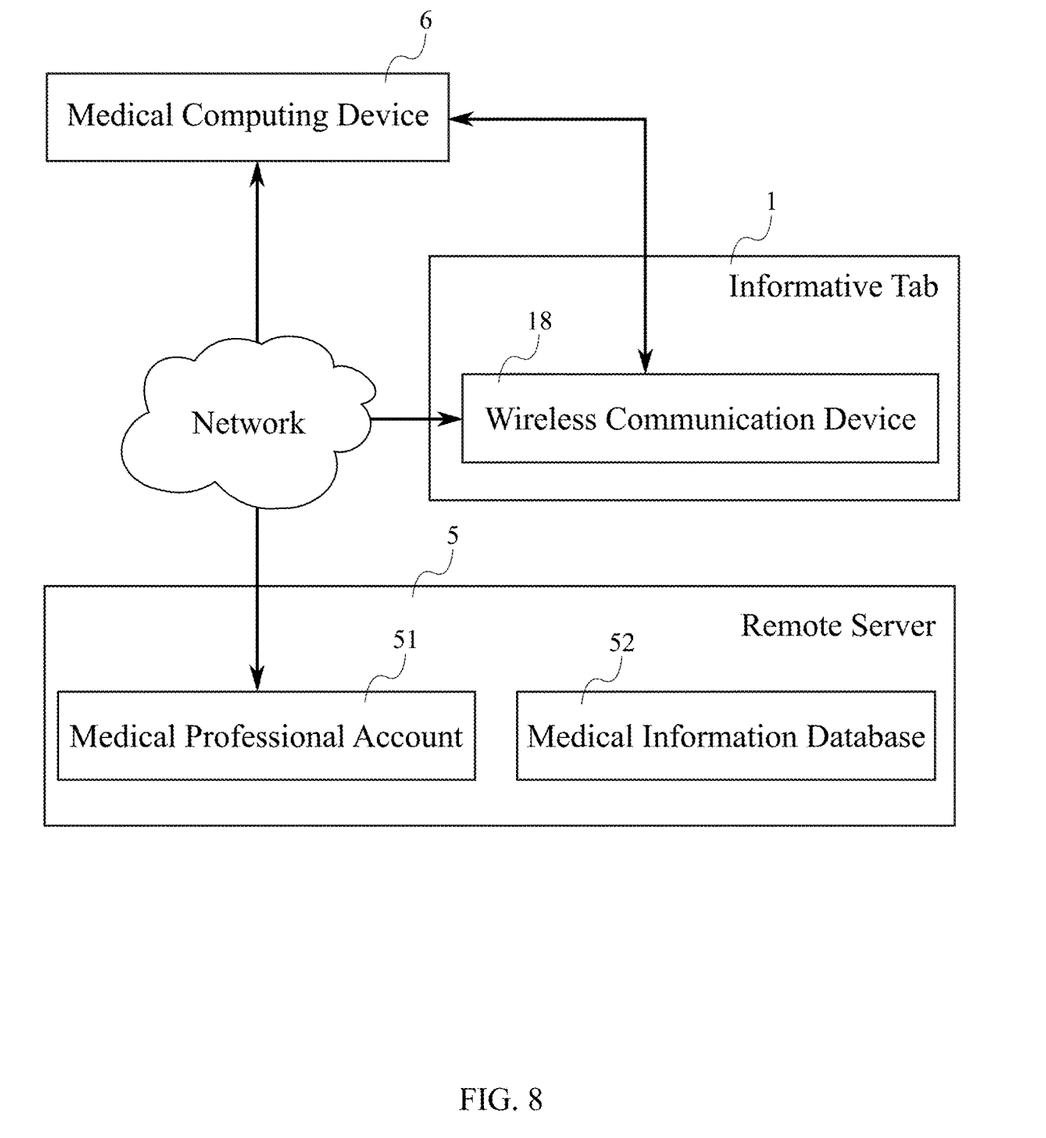
FIG. 8 is a box diagram illustrating communication between components of the present invention.
Figure 9:
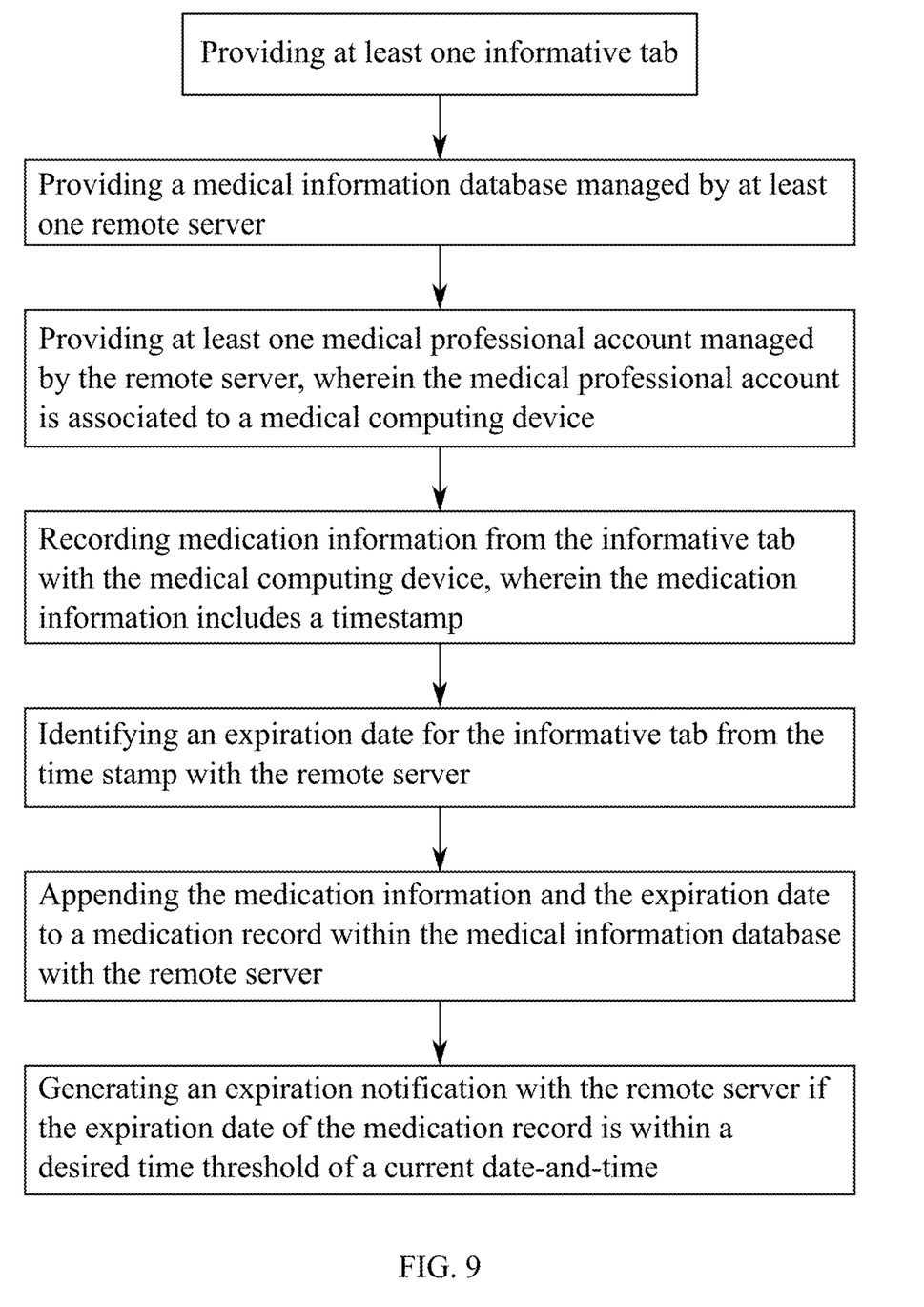
FIG. 9 is a flow diagram illustrating a process for tracking expiration dates and notifying medical professionals of important events using the present invention.
Figure 10:
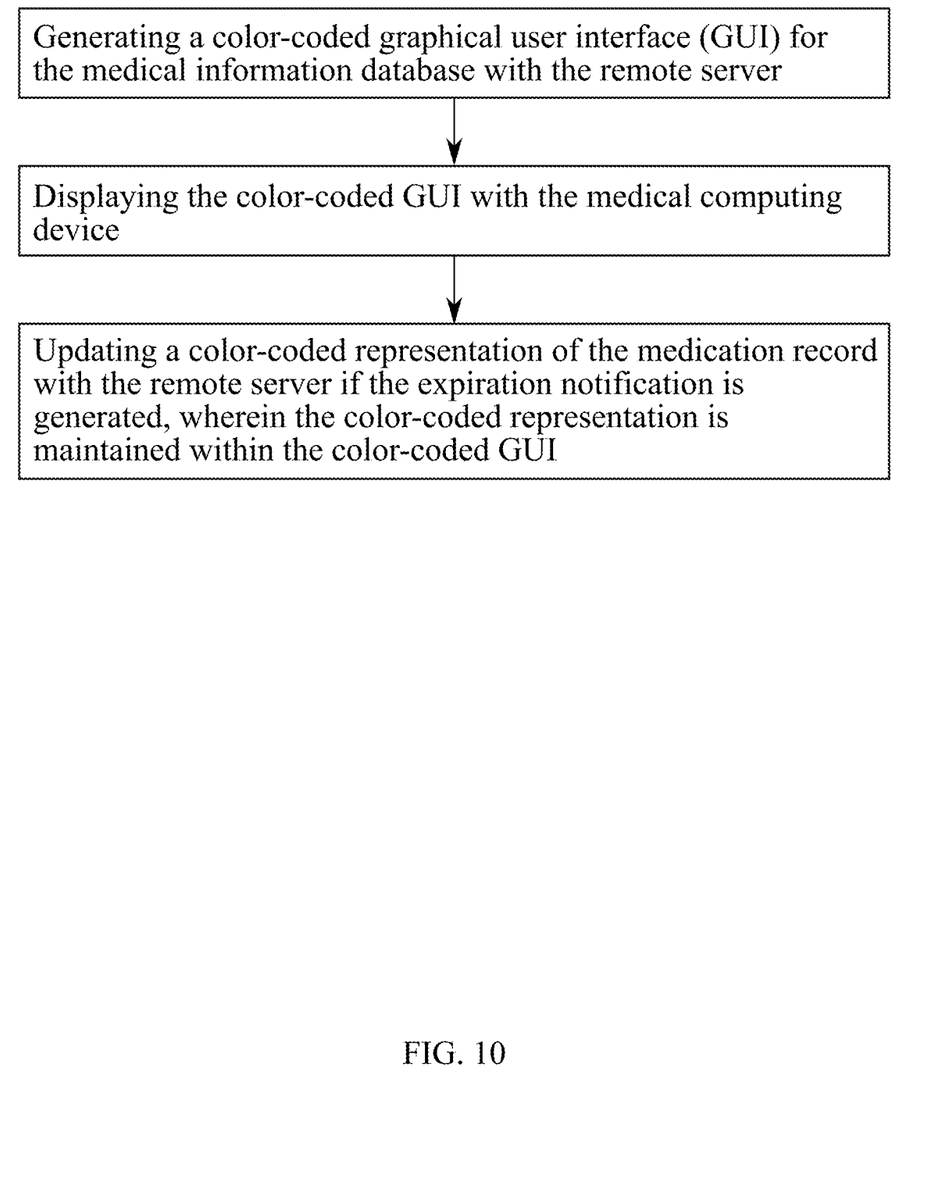
FIG. 10 is a flow diagram illustrating a process for generating a color-coded user interface based on expiration dates using the present invention.
Figure 11:
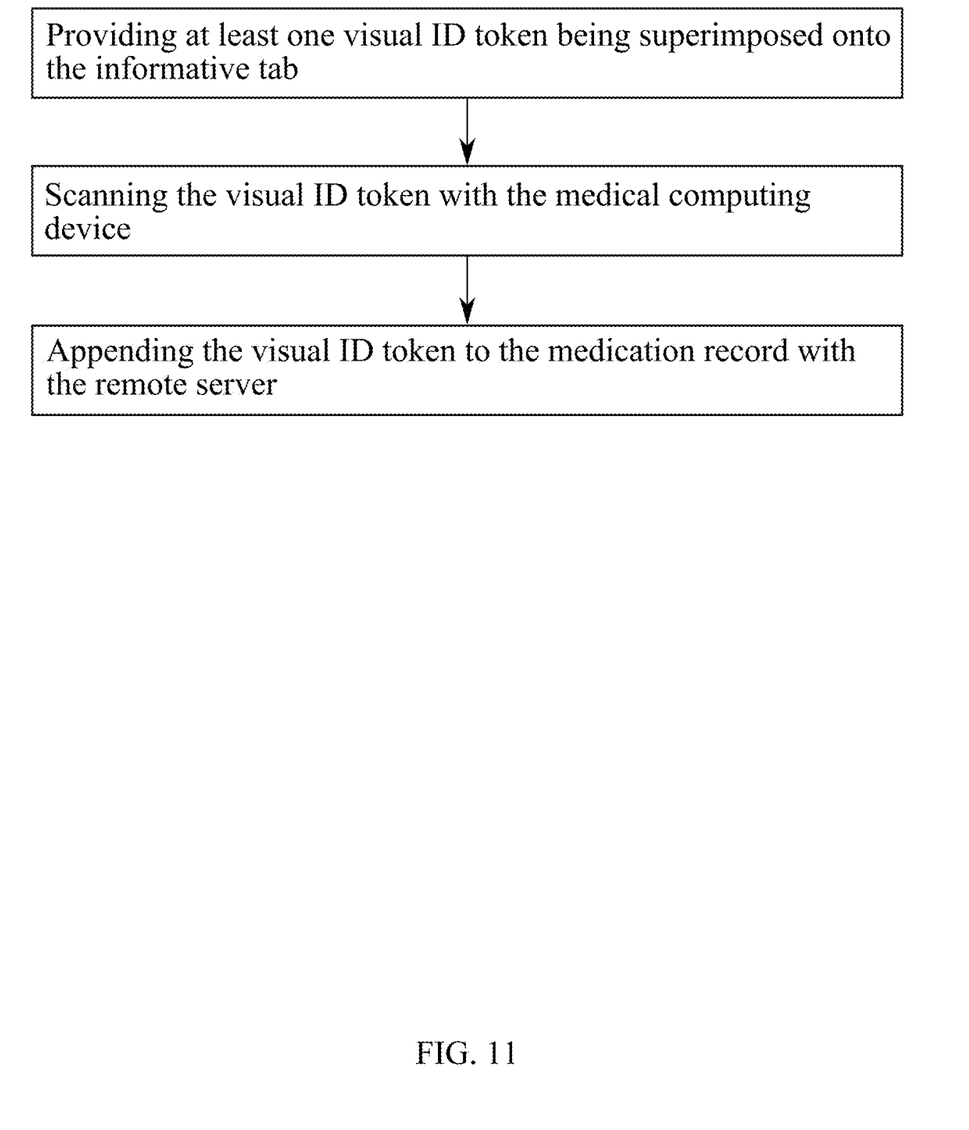
FIG. 11 is a flow diagram illustrating a process for appending visual ID tokens to a medication record using the present invention.
Figure 12:
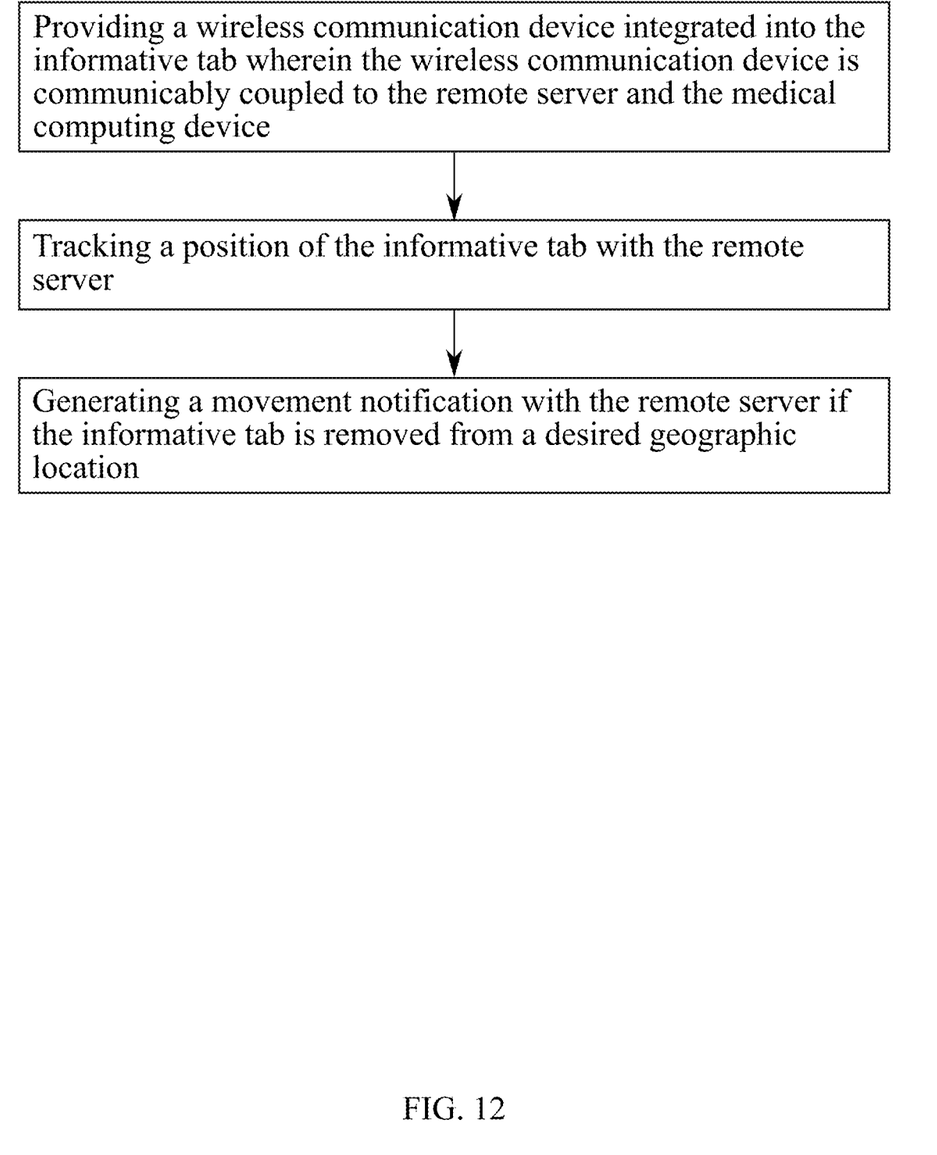
FIG. 12 is a flow diagram illustrating a process for tracking the physical location of a medication bottle using the present invention.

Referring to FIG. 2 and FIG. 8, the visual ID token 17 is a unique mark or symbol used to denote information about the medication bottle. To make use of this functionality, the visual ID token 17 is superimposed onto the medical information portion 12. Thus, the visual ID token 17 acts as a means of visually outputting information. Embodiments of the present invention make use of visual ID tokens 17 selected from the group including, but not limited to, QR codes, matrix barcodes, and serial numbers. The wireless communication device 18 is integrated into the informative tab 1 so that the medical professional can monitor the physical state and geographic location of the medication bottle. Embodiments of the present invention are equipped with wireless communication devices 18 selected from the group including, but not limited to, NFC, RFID, WIFI, GPS, and cellular networks Referring to FIG. 8, the system for tracking medication expiration dates comprises the above-described informative tab 1. The system further comprises a medical information database 52 managed by at least one remote server 5. The medical information database 52 refers to a searchable repository of medical information relating to specific medication bottles. Additionally, the medical information database 52 may include patient information, diagnosis data, medication information, and research data. The term remote server 5 is used herein to refer to a control system capable of storing medical information, coordinating communication between system components, and running any other background process is required to execute the system of the present invention. The system of the present invention further comprises at least one medical professional account 51 managed by the remote server 5. This medical professional account 51 is associated to a medical computing device 6. The term computing device is used herein to refer to any electronic device capable of performing the processing and communication operations required by the system of the present invention. Embodiments of the present invention employ computing devices selected from the group including, but not limited to, smart phones, tablet computers, smart watches desktop computers, and internet of things devices. The medical professional account 51 is a digital representation of a medical professional and enables the medical professional to access the electronic features of the system of the present invention.

Referring to FIG. 6 and FIG. 8, the system of the present invention is designed to enable the medical professional to electronically track medication expiration information. Because the system is sun using a remote server 5, the medical professional is able to access the data within the medication information database from multiple locations and devices. The medication tracking system begins by recording medication information from the informative tab 1 with the medical computing device 6. The medical information is the medication information and expiration date information disclosed on the medical information portion 12 and the expiration date portion 11. This medication information includes a timestamp that denotes the medication expiration date and the date the bottle was opened. The system continues by identifying an expiration date for the informative tab 1 from the time stamp with the remote server 5, and appending the medication information and the expiration date to a medication record within the medical information database 52 with the remote server 5. Thus, the medication record acts a digital repository for data associated to the medication bottle. To put it another way, the present invention begins tracking the medication bottle when the medical professional scans the visual ID token 17, manually records the visual ID token 17, or wirelessly connects to the informative tab 1. After the medical professional scans the visual ID token 17, the remote server 5 adds all the relevant information, including the visual ID token 17, about the medication bottle to the medical information database 52. Finally, the system generates an expiration notification with the remote server 5 if the expiration date of the medication record is within a desired time threshold of a current date-and-time. Thus, the present invention decrease the risk of using expired medication by notifying the medical professional when medication is expired or soon to expire. The present invention enables the medical professional to set the threshold, or the period of time, for when the expiration notification will be sent.

Referring to FIG. 8, preferably, the system of the present invention is used to track the medication information for a plurality of medication bottles. To facilitate this, the system of the present invention generates a color-coded graphical user interface (GUI) for the medical information database 52 with the remote server 5. The color-coded GUI is a dynamic representation of the medication record that can be accessed by a plurality of medical professionals, each of whom is using a corresponding medical computing device 6. Additionally, the medical professional can input, modify, and delete information within the medical information database 52 by interacting with the color-coded GUI. The system of the present invention enables the medical professional to interact with the color-coded GUI by displaying the color-coded GUI with the medical computing device 6. The system then continually updates a color-coded representation of the medication record with the remote server 5 if the expiration notification is generated. Thus, each medication record is tracked and the color for each record is modified depending on the period of time between the current date and time and the expiration date of the medication bottle. Additionally, the color-coded GUI can be updated whenever the medical professional scans in a new informative tab to create a new medication record. Further, the color-coded representation of the medication record can be changed based on a host of factors, including but not limited to, patient allergies, prescriber recommendations, medication interactions, and refill availability. The wireless communication device 18 is communicably coupled to the remote server 5 and the medical computing device 6. Accordingly, the remote server 5 and the medical computing device 6 are able to exchange information with the informative tab 1. In some embodiments, the present invention provides the feature of tracking a position of the informative tab 1 with the remote server 5. The system then generates a movement notification with the remote server 5 if the informative tab 1 is removed from a desired geographic location. Thus, the system of the present invention notifies the medical professional of unauthorized medication usage.

Although the invention has been explained in relation to its preferred embodiment, it is to be understood that many other possible modifications and variations can be made without departing from the spirit and scope of the invention as hereinafter claimed.

What is claimed is:

1. An injectable medication date tab comprising:
    an informative tab;
    release string;
    an adhesive liner;
    quick release fastener;
    the informative tab comprising an expiration date portion and a medical information portion;
    the expiration date portion being positioned adjacent to the medical information portion across a labeling surface of the informative tab;
    the adhesive liner being superimposed onto a mounting surface of the informative tab;
    the mounting surface being positioned opposite to the labeling surface across the informative tab; and
    the quick release fastener being connected in between the release string and a widthwise edge of the informative tab.

2. The injectable medication date tab as claimed in claim 1 further comprising: an adhesive strip; the release string comprising a cap tether and a tab-securing portion; quick release fastener being attached along the tab securing portion; the cap tether being positioned adjacent to the tab-securing portion along the release string; and the adhesive strip being superimposed onto the release string, opposite to the quick release fastener.

3. The injectable medication date tab as claimed in claim 2 further comprising: a cap-securing seal; and the cap tether being integrated into the cap-securing seal.

4. The injectable medication date tab as claimed in claim 2 wherein the cap-securing seal is a tamper-evident device.

5. The injectable medication date tab as claimed in claim 1 further comprising: a fold; the fold traversing across the informative tab; and the fold being positioned in between expiration date portion and the medical information portion.

6. The injectable medication date tab as claimed in claim 1 further comprising: an adhesive protector; the adhesive protector being positioned over a reattachment portion of the adhesive liner; and the reattachment portion being coextensive with the expiration date portion.

7. The injectable medication date tab as claimed in claim 1 further comprising: at least one visual identifier (ID) token; and the visual ID token being superimposed onto the medical information portion of the informative tab.

8. The injectable medication date tab as claimed in claim 7, wherein the visual ID token is a matrix barcode.

9. The injectable medication date tab as claimed in claim 1 further comprising: a wireless communication device; and the wireless communication device being integrated into the informative tab.

* * * * *